US006720309B1

(12) United States Patent
Janssens et al.

(10) Patent No.: US 6,720,309 B1
(45) Date of Patent: Apr. 13, 2004

(54) METHOD OF INDUCING VASODILATION AND TREATING PULMONARY HYPERTENSION USING ADENOVIRAL-MEDIATED TRANSFER OF THE NITRIC OXIDE SYNTHASE GENE

(75) Inventors: Stefan Janssens, Heverlee (BE); Kenneth D. Bloch, Brookline, MA (US); Désiré Collen, Winksele (BE)

(73) Assignees: Leuven Research and Development, V.Z.W., Leuven (BE); The General Hospital Corporation, Boston, MA (US)

( * ) Notice: Subject to any disclaimer, the term of this patent is extended or adjusted under 35 U.S.C. 154(b) by 0 days.

(21) Appl. No.: 08/896,053

(22) Filed: Jul. 17, 1997

Related U.S. Application Data
(60) Provisional application No. 60/021,912, filed on Jul. 17, 1996.

(51) Int. Cl.[7] .................. A61K 48/00; C12N 15/00; C12N 15/63; C12N 15/87
(52) U.S. Cl. ................ 514/44; 435/320.1; 435/325; 435/455; 435/456; 536/23.2; 424/93.2
(58) Field of Search .............................. 435/320.1, 325, 435/455, 456; 424/93.2; 536/23.2; 514/44

(56) References Cited

U.S. PATENT DOCUMENTS

| | | |
|---|---|---|
| 5,485,827 A | 1/1996 | Zapol et al. |
| 5,498,539 A | 3/1996 | Harrison et al. |

OTHER PUBLICATIONS

Heath (1993) Eur. Respir. Rev., vol. 3 (16), 555–558, 1993.*
Pietra (1994) Chest, vol. 105 (2 supp.) , 2S–7S, 1994.*
Chen et al. (1996) FASEB Journal., vol. 10(3), A303, Apr. 1996.*
Rosenfeld et al. (1992) Cell, vol. 68, 143–155, Jan. 1992.*
Janssens, S., et al., "Homogeneous myocardial expression of human constitutive nitric oxide synthase by adenoviral gene transfer during syngeneic heterotopic heart transplantation," *Circulation* 92:Abstract No. 2398, pp. I502, Lippincott, Williams & Wilkins (Oct. 1995).
Biosis Database, Accession No. 199698601285, from Thusu Kajori, G., et al., (Nov. 1995).
Biosis Database, Accession No. 199598495022, from Ziegler, J.W., et al., (Aug. 1995).
International Search Report for International patent application No. EP 97 93 3529, mailed Sep. 19, 2002.
Halbert, C.L., et al., "Retroviral Vectors Efficiently Transduce Basal and Secretory Airway Epithelial Cells In Vitro Resulting in Persistent Gene Expression in Organotypic Culture," *Human Gene Ther.* 7:1871–1881 (Oct., 1996).
Huang, P.L., and Fishman, M.C., "Genetic analysis of nitric oxide synthase isoforms: targeted mutation in mice," *J. Mol. Med.* 74:415–421 (1996).

Scott–Taylor, T.H., et al., "Adenovirus facilitated infection of human cells with ecotropic retrovirus," *Gene Ther.* 5:621–629 (1998).
Setoguchi, Y., et al., "Pathophysiology of the Respiratory System from the Viewpoint of Gene Expression, Transfer of Endothelial Nitric Oxide Synthase Gene in the Purpose of Gene Therapy for Pulmonary Arterial Hypertension," *Jap. Clin. Med.* (*Nihon Rinsho*) 54:89–96 (Feb. 1996).
English translation of: Setoguchi, Y., et al., "Pathophysiology of the Respiratory System from the Viewpoint of Gene Expression, Transfer of Endothelial Nitric Oxide Synthase Gene in the Purpose of Gene Therapy for Pulmonary Arterial Hypertension," *Jap. Clin. Med.* (*Nihon Rinsho*) 54:89–96 (Feb. 1996).
Tzeng, E., et al., "Vascular Gene Transfer of the Human Inducible Nitric Oxide Synthase: Characterization of Activity and Effects on Myointimal Hyperplasia," *Mol. Med.* 2:211–225 (Mar. 1996).*
Abu–Soud, H., et al., "Subunit Dissociation and Unfolding of Macrophage NO Synthase: Relationship between Enzyme Structure, Prosthetic Group Binding, and Catalytic Function," *Biochem.* 34:11167–11175 (1995).
Ballard, P.L., et al., "Adenovirus–mediated gene transfer to human fetal lung ex vivo," *Am. J. Physiol.* 268:L839–L845 (1995).
Bruner, L.H., et al., "The Effect of Immunosuppressants and Adoptive Transfer in Monocrotaline Pyrrole Pneumotoxicity," *Toxicol. Applied Pharmacol.* 91:1–12 (1987).
Budta, W., Circulation (2000) (In press).
Busconi, L., and Michel, T., "Endothelial Nitric Oxide Synthase Membrane Targeting," *J. Biol. Chem.* 269:25016–25020 (1994).
Chen, P.–F., et al., "Cysteine 99 of Endothelial Nitric Oxide Synthase (NOS–III) Is Critical for Tetrahydrobiopterin–Dependent MOS–III Stability and Activity," *Biochem. Biophys. Res. Commun.* 215:1119–1129 (1995).
Chen, P.–F., et al., "Cysteine 184 of Endothelial Nitric Oxide Synthase Is Involved in Heme Coordination and Catalytic Activity," *J. Biol. Chem.* 269:25062–25066 (1994).
Curiel, D.T., et al., "Gene Therapy Approaches for Inherited and Acquired Lung Diseases," *Am. J. Respir. Cell. Mol. Biol.* 14:1–18 (1996).

(List continued on next page.)

*Primary Examiner*—Anne M. Wehbé
(74) *Attorney, Agent, or Firm*—Sterne, Kessler, Goldstein & Fox P.L.L.C.

(57) ABSTRACT

This invention relates to a gene therapy method for inducing pulmonary vasodilation. More specifically, this invention involves introducing the nitric oxide synthase gene into lungs resulting in pulmonary vasodilation. This results in a hypotensive effect in the pulmonary circulation which does not significantly affect systemic blood pressure or cardiac index. This method is useful to treat primary pulmonary hypertension or pulmonary hypertension secondary to various disease states.

14 Claims, 7 Drawing Sheets

OTHER PUBLICATIONS

Crystal, R.G., "Gene Therapy Strategies for Pulmonary Disease," *Am. J. Med.* 92(*Supp. 6A*):6A–44S–6A–52S (1992).

Dahl, M., et al., "Ten Year Survival of a Patient with Advanced Pulmonary Hypertension and Mixed Connective Tissue Disease Treated with Immunosuppressive Therapy," *J. Rheum.* 19:1807–1809 (1992).

Dalesandro, J., et al., "Gene Therapy for Donor Hearts: Ex Vivo Liposome–Mediated Transfection," *J. Thorac. Cardio. Surgery* 111:416–422 (1996).

Degtyarenko, K.N., "Structural domains of P450–containing monooxygenase systems," *Protein Engin.* 8:737–747 (1995).

Garcia–Cardeña, G., et al., "Targeting of nitric oxide synthase to endothelial cell caveolae via palmitoylation: Implications for nitric oxide signalling," *Proc. Natl. Acad. Sci. USA* 93:6448–6453 (Jun. 1996).

Ghosh, D.K., et al., "Domains of macrophage NO Synthase Have Divergent Roles in Forming and Stabilizing the Active Dimeric Enzyme," *Biochem.* 35:1444–1449 (1996).

Gisslinger, H., et al., "Efficacy of cyclosporin A in systemic sclerosis," *Clin: Exp. Rheum.* 9:383–390 (1991).

Greenberg, M.L., et al., "Long–term hemodynamic follow–up of cardiac transplant patients treated with cyclosporine and prednisone," *Circulation* 71:487–494 (1985).

Hales, C.A., "The Site and mechanism of Oxygen Sensing for the Pulmonary Vessels," *Chest* 88(*Suppl.*):235S–240S (1985).

Hodgson, C.P., and Solaiman, F., "Virosomes: Cationic Liposomes enhance Retroviral Transduction," *Nature Biotechnol.* 14:339–342 (1996).

Lee, M.–E., et al., "Functional Analysis of the Endothelin–1 Gene Promoter," *J. Biol. Chem.* 265:10446–10450 (1990).

Lee, C.M., et al., "Oligomerization of Endothelial Nitric Oxide Synthase," *J. Biol. Chem.* 270:27403–27406 (1995).

Lemarchand, P., et al., "In vivo adenovirus–mediated gene transfer to lungs via pulmonary artery," *J. Applied Phys.* 76:2840–2845 (1994).

Liu, J., and Sessa, W.C., "Identification of Covalently Bound Amino–terminal Myristic Acid in Endothelial Nitric Oxide Synthase," *J. Biol. Chem.* 269:11691–11694 (1994).

Liu, J., et al., "Biosynthesis of Palmitoylation of Endothelial Nitric Oxide Synthase: Mutagenesis of Palmitoylation Sites, Cysteines–15 and/or –26, Argues against Depalmitoylation–Induced Translocation of the Enzyme," *Biochem.* 34:12333–12340 (1995).

Mathieu, P., et al., "L–Arginine Prevents Cyclosporin A–Induced Pulmonary Vascular Dysfunction," *Ann. Thorac. Surg.* 64:414–420 (1997).

Morelli, S., et al., "Pulmonary Arterial Hypertension Responsive to Immunosuppressive Therapy in Systemic Lupus Erythematosus," *Lupus* 2:367–369 (1993).

Nishimura, J.S., et al., "Modular Structure of Neuronal Nitric Oxide Synthase: Localization of the Arginine Binding Site and Modulation by Pterin," *Biochem. Biophys. Res. Commun.* 210:288–294 (1995).

Padeh, S., et al., "Primary Pulmonary Hypertension in a Patient with Systemic–Onset Juvenile Arthritis," *Arthritis Rheum.* 34:1575–1579 (1991).

Qiu, P., et al., "Gene gun delivery of mRNA in situ results in efficient transgene expression and genetic immunization," *Gene Ther.* 3:262–268 (1996).

Adnot, S., et al., "Loss of Endothelium–dependent Relaxant Activity in the Pulmonary Circulation of Rats Exposed to Chronic Hypoxia," *J. Clin. Invest.* 87:155–162 (1991).

Assender, J.W., et al., "Does Nitric Oxide Inhibit Smooth Muscle Proliferation?," *J. Cardiovasc. Pharmacol.* 17(*Suppl. 3*):S104–S107 (1991).

Bernstein, A., et al., "Gene Transfer with Retrovirus Vectors," in: *Genetic Engineering: Principles and Methods*, vol. 7, Setlow, J.K., and Hollaender, A., eds., Plenum Press; New York, pp. 235–261 (1985).

\* cited by examiner

```
gaattcccactctgctgctccagacgagacgacgcacagtaacatgggcaacttgaagagcgtggcccaggagcctg
ggccaccctgcgcctggggctgggcttggcttgcggctgtgcggcaagcaggcccagccaccccggccctgagccc
agccgggcccagcatccctactcccaccagcgccagaacagcccgagctccccgctaaccagccccagagg
gccaagttccctgtgtgaagaactgggaggtgggagcatcacctatgacgaaactcagcgcccagcgcagcaggatg
ggccctgcaccccaagacgctgctgggctgggctcccggactcctgtatttccacggaaactacaggcgccctccccgcccccg
gccctgagcgctgctgagtcaggcccggagcttcatcaaccagtactacagctccattaagaggagcggctcccagc
cacgaacagcggcttcaagaggtggaagcgagctgccagtggcagccaccaggccacctaccagcttaggagagcgagctggtgt
tcgggctaagcaggcctgcgcacagcctccccgctgcgtgggccggatccagtggggaagctgcaggtgttgatgcc
cggactgcaggtctgcacagtgttccgcagcgctgcccggccctgcgggggaccccagccaaacgtggaacagccagctgcgctacg
ctcggccatcacagtgttccgcagcgctgcccggccctgcgggggaccccagccaacgtggagatcaccgagctctgcattcagcggc
cgggctaccggcagcagcaggacggctctgtgcgggggaccccagccaacgtggagatcaccgagctctgcattcagcggc
tggaccccagaaacggtcgttcgttgagtgccctggagcaccaccgcaggtcctccagtgtgtttgcagcctggcctgcgctgtacg
gccccccgagctggtcttgagtgccaacatgctgctggaaattggggcttgctgaaattgggggcctgagttcccgagccccttcagtggcctgtacatg
cctcccggcagtgccaacatgctgctgctgctgaaattgggggcctgagttcccgagccccttcagtggcctggtgtctgcacagttaccagc
agcactgagatcggcacgaggaacctgtgtgaccctcaccgctacaacatcctggaggatgtggctgtgctgcacagttaccagc
ggataccggaccactctgtccctgtggaaagacaaggcagcagtgaaatcaacgtggccgtgctgctgcacagttaccagc
tagccaaagtcaccatcacgtggaccaccacgcgccacggcctctcttcatgaagcacctggaagatgagcagaaggcagg
ggggctgccctgcagactgggctgatcgtgccccatctcggccagctcactcctgttttccatcaggagatggt
caactatttcctgtcccgccttccgctaccagccagacgcgtgaagatctccgctcatgggcacgtgatggcgaagcgagtg
gaagagaccttaaagagtgcaacgcgtggccgggaccgcgggaccgccagactacgcagcagcagcggggagactcttccgaaggc
aaggcgacaatcctgtatgctccgagaccgcgggaccgccagactacgcagcagcagcggggagactcttccgaaggc
tttgatcccgggtcctgtatgtgatgagtgacgtggtgtccctcgaacacgagacgctggtgctggtggtaacca
gcacatttggaatgggatccccggagacagcacaagacttgcgctgagatgtccgcccctacaac
agctccccctcggcggaacagcacaagagttataagatccgcttcaacagcatctcctgctcagacccactggtcctc
ttgcggcggaagaggaagcagtcagtaacacagacagtgcagggcccctgcaggccctgcaccccactgtgtttcgggc
tcggctcccgggcataccccactttctgccttttgctgccgtggacacacggctgggaggaactggggcgggagcgg
```

FIG.6A

```
ctgctgcagctgggccagggcgacgagctgtgcggccaggaggaggccttccgagctgggctgggccagctgccttccagc
cgcctgtgagacctttctgtgtgggagaggatgccaaggccgccgccgaggccctcagcccaaacgagctggaagc
gccagaggtaccggctgagcgccgagggcctgcagttgctgccagtctgatccacgtgacaggcggaagatg
ttccaggctacaatccgtcagtggaaaacctgcaaagcagcaagcaccatagttctgccgccaccctgtgcgctgacac
cggaggccagaggggctgcagtaccagtcggggaccacatagttctgccgccaaccggccctgtgggagg
cgctgctgagccgcgtggaggacccgcggccgcccactgagccctggcagtagagcagtggagaagggcagccctggt
ggccctcccccggctggtgcgggaccccccggctgccctgtgacgctgccaggctctcaccttcttcctggacat
cacctcccacccagctcttgcggctgtcctcagctcttggcagaagagcccaggaacagcaggagctggagg
ccctcagccaggatcccgacgctacgagagtggaagtggttccgctgccctgtgagctgctggagcagttc
ccgtcggtggcgctgccccactgctcctcaccagctgtcgtgcatacaggactcaggatggctgggccccctgc
accagcaccaccaagagatccacctcactgtagctgtgctggagacccctgtgcctgcttcatccgggggctcctcc
actatggagtctgctccacgtggctaagcagtcagctgccctgcatccaggacctgccctactgggggctccccctc
ttccggctgccacccaccagctgccctgcatccgatccagctctgcctggggtcaggcactgactttggtgttcgctgccgatgctccc
gcaggagcggctgcatgacattgaggacgaaagggctgcagccactccatgactttggtgttcgctgccgatgctccc
aacttgaccatctctaccgacgaggtgcagaacgcccagcagcgcgggtgtttggccgagtcctcaccgccttctcc
cggaacctgacaacccaagacatgtttgtctgcggcgaggtggcagaggacatcctgaggacggagctgcgcgtgctgtg
cctcgagcggggcgacatggagctggacaccagaggtgacaagccgcatacgcaccaccagagcttttcctgcaggagcgtcagtt
cgacggagggcgacatggagctggacaccagaggtgacaagccgcatacgcaccaccagagcccctgctttccctctcc
atttcggctcacgctgccaccagaggtgacaagccgacatacgcaccaccagagcccctgctttccctctcc
gcggggcgagtgcctgggctgacccctgcggccctgcgacaccacagccccgtcctcccctttgaggtgtgccttt
agttccggagagcggctgcccgactcagttcgccgactcagttcagatttcctccaggaggacaaaacgctctttcctctctaggc
ctcacatctgtccagaggctgcaagatcagattccagattcctccaggaggacaaaacgctctttcctctctaggc
ctgttgcctgggctggctccgcgttagttagatctcgatttcctccaggagtatcttacctgtaaagtctaatctctaatca
tcctgtttcttagtccgaatgttagattagattttcctcttgcctcttgcctcttgtaaagtactactaaagtgctacccagctcaa
agtattattattgaagattaccataaggactgtccagatgttaggagaactactaaagtgctacccagctcaa
aaaaaaaaaaaaaaa
```

FIG. 6B

```
                          SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:1:

CGGCGATGTT ACCATGGCAA CCAACGT                                          27

(2) INFORMATION FOR SEQ ID NO:2:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:2:

CGGATCCCGG CTCTCAGGGG CTGTTGGTG                                        29

(2) INFORMATION FOR SEQ ID NO:3:

(i) SEQUENCE CHARACTERISTICS:
           (A) LENGTH: 27 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:3:

CGGCGATGTT ACCATGGCAA CCAACGT                                          27

(2) INFORMATION FOR SEQ ID NO:4:

(i) SEQUENCE CHARACTERISTICS:
           (A) LENGTH: 20 base pairs
           (B) TYPE: nucleic acid
           (C) STRANDEDNESS: single
           (D) TOPOLOGY: linear (ii) MOLECULE TYPE: cDNA (xi) SEQUENCE DESCRIPTION: SEQ ID NO:4:

CTCTGTAGGT AGTTTGTCCA                                                  20
```

(2) INFORMATION FOR SEQ ID NO:5:

(i) SEQUENCE CHARACTERISTICS:
        (A) LENGTH: 4099 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

```
GAATTCCCAC TCTGCTGCCT GCTCCAGCAG ACGGACGCAC AGTAACATGG GCAACTTGAA      60

GAGCGTGGCC CAGGAGCCTG GGCCACCCTG CGGCCTGGGG CTGGGGCTGG GCCTTGGGCT     120

GTGCGGCAAG CAGGGCCCAG CCACCCCGGC CCCTGAGCCC AGCCGGGCCC CAGCATCCCT     180

ACTCCCACCA GCGCCAGAAC ACAGCCCCCC GAGCTCCCCG CTAACCCAGC CCCCAGAGGG     240

GCCCAAGTTC CCTCGTGTGA AGAACTGGGA GGTGGGGAGC ATCACCTATG ACACCCTCAG     300

CGCCCAGGCG CAGCAGGATG GGCCCTGCAC CCCAAGACGC TGCCTGGGCT CCCTGGTATT     360

TCCACGGAAA CTACAGGGCC GGCCCTCCCC CGGCCCCCCG GCCCCTGAGC AGCTGCTGAG     420

TCAGGCCCGG GACTTCATCA ACCAGTACTA CAGCTCCATT AAGAGGAGCG GCTCCCAGGC     480

CCACGAACAG CGGCTTCAAG AGGTGGAAGC CGAGGTGGCA GCCACAGGCA CCTACCAGCT     540

TAGGGAGAGC GAGCTGGTGT TCGGGCTAAG CAGGCCTGG CGCAACGCTC CCCGCTGCGT     600

GGGCCGGATC CAGTGGGGGA AGCTGCAGGT GTTCGATGCC CGGGACTGCA GGTCTGCACA     660

GGAAATGTTC ACCTACATCT GCAACCACAT CAAGTATGCC ACCAACCGGG GCAACCTTCG     720

CTCGGCCATC ACAGTGTTCC CGCAGCGCTG CCCTGGCCGA GGAGACTTCC GAATCTGGAA     780

CAGCCAGCTG GTGCGCTACG CGGGCTACCG GCAGCAGGAC GGCTCTGTGC GGGGGGACCC     840

AGCCAACGTG GAGATCACCG AGCTCTGCAT TCAGCACGGC TGGACCCCAG GAAACGGTCG     900

CTTCGACGTG CTGCCCCTGC TGCTGCAGGC CCCAGATGAG CCCCCAGAAC TCTTCCTTCT     960

GCCCCCCGAG CTGGTCCTTG AGGTGCCCCT GGAGCACCCC ACGCTGGAGT GGTTTGCAGC    1020

CCTGGGCCTG CGCTGGTACG CCCTCCCGGC AGTGTCCAAC ATGCTGCTGG AAATTGGGGG    1080

CCTGGAGTTC CCCGCAGCCC CCTTCAGTGG CTGGTACATG AGCACTGAGA TCGGCACGAG    1140

GAACCTGTGT GACCCTCACC GCTACAACAT CCTGGAGGAT GTGGCTGTCT GCATGGACCT    1200

GGATACCCGG ACCACCTCGT CCCTGTGGAA AGACAAGGCA GCAGTGGAAA TCAACGTGGC    1260

CGTGCTGCAC AGTTACCAGC TAGCCAAAGT CACCATCGTG GACCACCACG CCGCCACGGC    1320

CTCTTTCATG AAGCACCTGG AGAATGAGCA GAAGGCCAGG GGGGGCTGCC CTGCAGACTG    1380

GGCCTGGATC GTGCCCCCCA TCTCGGGCAG CCTCACTCCT GTTTTCCATC AGGAGATGGT    1440

CAACTATTTC CTGTCCCCGG CCTTCCGCTA CCAGCCAGAC CCCTGGAAGG GGAGTGCCGC    1500

CAAGGGCACC GGCATCACCA GGAAGAAGAC CTTTAAAGAA GTGGCCAACG CCGTGAAGAT    1560

CTCCGCCTCG CTCATGGGCA CGGTGATGGC GAAGCGAGTG AAGGCGACAA TCCTGTATGG    1620

CTCCGAGACC GGCCGGGCCC AGAGCTACGC ACAGCAGCTG GGGAGACTCT TCCGGAAGGC    1680

TTTTGATCCC CGGGTCCTGT GTATGGATGA GTATGACGTG GTGTCCCTCG AACACGAGAC    1740

GCTGGTGCTG GTGGTAACCA GCACATTTGG GAATGGGGAT CCCCCGGAGA ATGGAGAGAG    1800

CTTTGCAGCT GCCCTGATGG AGATGTCCGG CCCCTACAAC AGCTCCCCTC GGCCGGAACA    1860

GCACAAGAGT TATAAGATCC GCTTCAACAG CATCTCCTGC TCAGACCCAC TGGTGTCCTC    1920

TTGGCGGCGG AAGAGGAAGG AGTCCAGTAA CACAGACAGT GCAGGGGCCC TGGGCACCCT    1980
```

-continued

```
CAGGTTCTGT GTGTTCGGGC TCGGCTCCCG GGCATACCCC CACTTCTGCG CCTTTGCTCG    2040
TGCCGTGGAC ACACGGCTGG AGGAACTGGG CGGGGAGCGG CTGCTGCAGC TGGGCCAGGG    2100
CGACGAGCTG TGCGGCCAGG AGGAGGCCTT CCGAGGCTGG GCCCAGGCTG CCTTCCAGGC    2160
CGCCTGTGAG ACCTTCTGTG TGGGAGAGGA TGCCAAGGCC GCCGCCCGAG ACATCTTCAG    2220
CCCCAAACGG AGCTGGAAGC GCCAGAGGTA CCGGCTGAGC GCCCAGGCCG AGGGCCTGCA    2280
GTTGCTGCCA GGTCTGATCC ACGTGCACAG GCGGAAGATG TTCCAGGCTA CAATCCGCTC    2340
AGTGGAAAAC CTGCAAAGCA GCAAGTCCAC GAGGGCCACC ATCCTGGTGC GCCTGGACAC    2400
CGGAGGCCAG GAGGGGCTGC AGTACCAGCC GGGGGACCAC ATAGGTGTCT GCCCGCCCAA    2460
CCGGCCCGGC CTTGTGGAGG CGCTGCTGAG CCGCGTGGAG GACCCGCCGG CGCCCACTGA    2520
GCCCGTGGCA GTAGAGCAGC TGGAGAAGGG CAGCCCTGGT GGCCCTCCCC CCGGCTGGGT    2580
GCGGACCCC CGGCTGCCCC CGTGCACGCT GCGCCAGGCT CTCACCTTCT TCCTGGACAT    2640
CACCTCCCCA CCCAGCCCTC AGCTCTTGCG GCTGCTCAGC ACCTTGGCAG AAGAGCCCAG    2700
GGAACAGCAG GAGCTGGAGG CCCTCAGCCA GGATCCCCGA CGCTACGAGG AGTGGAAGTG    2760
GTTCCGCTGC CCCACGCTGC TGGAGGTGCT GGAGCAGTTC CCGTCGGTGG CGCTGCCTGC    2820
CCCACTGCTC CTCACCCAGC TGCCTCTGCT CCAGCCCCGG TACTACTCAG TCAGCTCGGC    2880
ACCCAGCACC CACCCAGGAG AGATCCACCT CACTGTAGCT GTGCTGGCAT ACAGGACTCA    2940
GGATGGGCTG GGCCCCCTGC ACTATGGAGT CTGCTCCACG TGGCTAAGCC AGCTCAAGCC    3000
CGGAGACCCT GTGCCCTGCT TCATCCGGGG GGCTCCCTCC TTCCGGCTGC CACCCGATCC    3060
CAGCTTGCCC TGCATCCTGG TGGGTCCAGG CACTGGCATT GCCCCCTTCC GGGGATTCTG    3120
GCAGGAGCGG CTGCATGACA TTGAGAGCAA AGGGCTGCAG CCCACTCCCA TGACTTTGGT    3180
GTTCGGCTGC CGATGCTCCC AACTTGACCA TCTCTACCGC GACGAGGTGC AGAACGCCCA    3240
GCAGCGCGGG GTGTTTGGCC GAGTCCTCAC CGCCTTCTCC CGGGAACCTG ACAACCCCAA    3300
GACCTACGTG CAGGACATCC TGAGGACGGA GCTGGCTGCG GAGGTGCACC GCGTGCTGTG    3360
CCTCGAGCGG GGCCACATGT TTGTCTGCGG CGATGTTACC ATGGCAACCA ACGTCCTGCA    3420
GACCGTGCAG CGCATCCTGG CGACGGAGGG CGACATGGAG CTGGACGAGG CCGGCGACGT    3480
CATCGGCGTG CTGCGGGATC AGCAACGCTA CCACGAAGAC ATTTTCGGGC TCACGCTGCG    3540
CACCCAGGAG GTGACAAGCC GCATACGCAC CCAGAGCTTT TCCTTGCAGG AGCGTCAGTT    3600
GCGGGGCGCA GTGCCCTGGG CGTTCGACCC TCCCGGCTCA GACACCAACA GCCCCTGAGA    3660
GCCGCCTGGC TTTCCCTTCC AGTTCCGGGA GAGCGGCTGC CCGACTCAGG TCCGCCCGAC    3720
CAGGATCAGC CCCGCTCCTC CCCTCTTGAG GTGGTGCCTT CTCACATCTG TCCAGAGGCT    3780
GCAAGGATTC AGCATTATTC CTCCAGGAAG GAGCAAAACG CCTCTTTTCC CTCTCTAGGC    3840
CTGTTGCCTC GGGCCTGGGT CCGCCTTAAT CTGGAAGGCC CCTCCCAGCA GCGGTACCCC    3900
AGGGCCTACT GCCACCCGCT TCCTGTTTCT TAGTCCGAAT GTTAGATTCC TCTTGCCTCT    3960
CTCAGGAGTA TCTTACCTGT AAAGTCTAAT CTCTAAATCA AGTATTTATT ATTGAAGATT    4020
TACCATAAGG GACTGTGCCA GATGTTAGGA GAACTACTAA AGTGCCTACC CCAGCTCAAA    4080
AAAAAAAAAA AAAAAAAA                                                  4099
```

METHOD OF INDUCING VASODILATION AND TREATING PULMONARY HYPERTENSION USING ADENOVIRAL-MEDIATED TRANSFER OF THE NITRIC OXIDE SYNTHASE GENE

CROSS REFERENCE TO RELATED APPLICATION

This application claims the benefit of U.S. Provisional Application No. 60/021,912, filed Jul. 17, 1996, which is hereby incorporated by reference.

STATEMENT AS TO RIGHTS TO INVENTIONS MADE UNDER FEDERAL SPONSORED RESEARCH AND DEVELOPMENT

Part of the work performed during development of this invention was supported by U.S. Government funds. The U.S. Government may have certain rights in this invention.

BACKGROUND OF THE INVENTION

1. Field of the Invention

This invention relates to a gene therapy method for inducing pulmonary vasodilation by transducing a nitric oxide synthase gene into lung tissue. This invention also relates to methods of treating pulmonary hypertension and pharmaceutical compositions for treating pulmonary hypertension.

2. Related Art

Blood flow through the pulmonary circulation is highly regulated. For example, the pulmonary endothelium regulates pulmonary blood flow and maintains a low vascular resistance by releasing vasoactive substances, which control vasomotor tone, vascular patency, and normal vessel wall architecture. Vanhoutte, *N. Engl. J. Med.* 319:512–513 (1988).[1] Vasomotor tone relates to the degree of active tension in the vessel wall and partially determines the luminal diameter of the vessel. Vascular patency refers to the condition of a blood vessel where the internal luminal diameter is normal and blood flow is unimpeded.

[1] This article and all other articles, patents, or other documents cited or referred to in this application are specifically incorporated herein by reference.

Nitric oxide is one compound that plays an important role in regulating pulmonary blood flow. However, it is a gas with no known storage mechanism, which diffuses freely across membranes and is extremely labile. Nitric oxide has a biological half-life on the order of seconds, and its production is tightly regulated.

Nitric oxide is produced by two classes of nitric oxide synthases (NOS). Nathan, *FASEB J.* 6:3051–3064 (1992). The constitutively expressed nitric oxide synthases, exist as two isoforms: the endothelial nitric oxide synthase (ceNOS) and the neuronal nitric oxide synthase, (nNOS). These isoforms are expressed in vascular endothelial cells, platelets, and in neural tissues such as the brain. This class of nitric oxide synthase is calcium and calmodulin dependent. In blood vessels ceNOS mediates endothelium dependent vasodilation in response to acetylcholine, bradykinin, and other mediators. Nitric oxide levels increase in response to shear stress, i.e., forces on the blood vessels in the direction of blood flow, and the mediators of inflammation. Furchgott and Vanhoutte, *FASEB J.* 3:2007–2018 (1989); Ignarro, *FASEB J.* 3:31–36 (1989).

In the nervous system, the neuronal NOS isoform is localized to discrete populations of neurons in the cerebellum, olfactory bulb, hippocampus, corpus striatum, basal forebrain, and brain stem. Bredt et al., *Nature* 347:768–770 (1990). Neuronal NOS is also concentrated in the posterior pituitary gland, in the superoptic and paraventricular hypothalmic nuclei, and in discrete ganglion cells of the adrenal medulla Id. The widespread cellular localization of the neuronal NOS isoform and the short half-life and diffusion properties of nitric oxide suggest that NOS plays a role in nervous system morphogenesis and synaptic plasticity.

The second class, inducible nitric oxide synthase (iNOS), is expressed in macrophages, hepatocytes, and tumor cells. Steuhr et al., *Adv. Enzymol. Relat. Areas Mol. Biol.* 65:287–346 (1992); Lowenstein et al., *Proc. Natl. Acad. Sci. (USA)* 89:6711–6715 (1992). The inducible form of NOS is not calcium regulated, but its expression is induced by cytokines. This form of NOS functions as a cytotoxic agent, and NO produced by inducible NOS targets tumor cells and pathogens. Hibbs et al., *Biochem. Biophys. Res. Comm.* 157:87–94 (1988); Nathan, *FASEB J.* 6:3051–3064 (1992); Marletta, *Trends Biochem. Sci.* 14:488–492 (1989).

All isoforms of NOS catalyze the conversion of L-arginine to L-citrulline with production of NO. In vascular smooth muscle cells and in platelets, NO activates soluble guanylate cyclase, which increases intracellular guanosine 3',5'-cyclic monophosphate (cGMP), thereby inducing vasorelaxation and inhibiting platelet aggregation. The antiplatelet effect of NO and its vasodilatory and anti-proliferative action on pulmonary vascular smooth muscle cells suggest that NO may be an important modulator of pulmonary hypertension. Moncada et al., *Pharmacol. Res.* 43:109–142 (1991); Garg et al., *J. Clin. Invest.* 83:1774–1777 (1989); Roberts et al., *Circ. Res.* 76:215–222 (1995); Heath, *Eur. Respir. Rev.* 3:555–558 (1993); Radomski et al., *Biochem. Biophys. Res. Commum.* 148:1482–1489 (1987); Assender et al., *J. Cardiovasc. Pharmacol.* 17:104–107 (1991); de Graaf et al., *Circulation* 85:2284–2290 (1992).

The sequence of the various NOS isoforms have been published or are available in Genbank under the following accession numbers:

|  | Species: | | | |
| --- | --- | --- | --- | --- |
| Gene: | Man | Rat | Mouse | Cow |
| Neuronal | U17327 | X59949 | D14552 | |
|  | D16408 | | | |
|  | L02881 | | | |
| Macrophage (iNOS) | L09210 | D14051 | M87039 | U18331 |
|  | X85759-81 | D83661 | U43428 | U14640 |
|  | U18334 | U26686 | L23806 | |
|  | U31511 | U16359 | L09126 | |
|  | U20141 | D44591 | M92649 | |
|  | U05810 | X76881 | M84373 | |
|  | X73029 | U02534 | | |
|  | L24553 | L12562 | | |
| Endothelial | X76303-16 | U18336 | | M89952 |
|  | L26914 | U28933 | | L27056 |
|  | L23210 | | | M95674 |
|  | L10693 | | | M99057 |
|  | M95296 | | | M89952 |
|  | M93718 | | | |

Each of these sequences are expressly incorporated herein by reference. The different forms of NOS are about 50 to 60 percent homologous overall.

Several in vitro and in vivo results suggest that NO may play a role in the pulmonary vascular response to hypoxia. For example, in perfused isolated lungs, hypoxia induces a significant reduction in contractile responses to acetylcholine and to inhibitors of NOS. Adnot et al., *J. Clin. Invest.* 87:155–162 (1991). In isolated pulmonary vascular rings hypoxia suppresses basal and agonist-stimulated release of NO. Johns et al., *Circ. Res.* 65:1508–1515 (1989); Shaul et al., *J. Cardiovasc. Pharmacol.* 22:819–827 (1993). In endothelial cells, hypoxia inhibits NO production by reducing ceNOS mRNA levels and ceNOS mRNA stability. McQuillan et al., *Am J. Physiol.* 267:H1921–H1927 (1994). Moreover, downregulation of ceNOS mRNA and protein correlate inversely with the severity of the plexogenic pulmonary arteriopathy in the lungs of patients with pulmonary hypertension. Giaid et al., *N. Engl. J. Med.* 333:214–221 (1995). Therefore, hypoxia-induced hypertension may correlate with reduced NO generation from pulmonary endothelium affecting the balance between pulmonary vasoconstrictive and vasodilatory stimuli.

In addition to hypoxia-induced pulmonary hypertension, there are other forms of pulmonary hypertension. For example, pulmonary hypertension can result from disease states such as interstitial lung diseases with fibrosis, e.g., sarcoidosis and pneumoconioses, e.g., silicosis. Pulmonary hypertension on can also result from emboli, from parasitic diseases such as schistosomiasis or filariosis, from multiple pulmonary artery thromboses associated with sickle cell disease, and from cardiac disease, such as cor pulmonale, and from ischemic and valvular heart disease.

In addition to resulting from other disease, pulmonary hypertension can also be a primary disease condition. Primary pulmonary hypertension is an uncommon disease, which can only be diagnosed after a thorough search for the usual causes of pulmonary hypertension. Ordinarily, the natural course of this disease encompasses about five years, and it is normally fatal, with treatment being palliative. While pharmacological vasodilator therapy for primary and secondary pulmonary hypertension is known, these methods often have undesirable systemic hypotensive side effects.

The use of gene therapy for the treatment of various diseases and disorders has advanced significantly over the last several years. In contrast to traditional pharmaceuticals, gene therapy refers to the transfer and insertion of new genetic information into cells or the substitution of deficient genetic information for the therapeutic treatment of diseases or disorders. In some cases the gene is expressed in the target cell, while in other cases expression is not required, e.g., antisense technology. The foreign gene is normally transferred into a cell that proliferates to spread the new gene throughout the cell population. Often stem cells or pluripotent progenitor cells are the target of gene transfer since they proliferate to various progeny lineages that may express the foreign gene.

High efficiency gene transfer systems for hematopoietic progenitor cell transformation have been described. See Morrow, *Ann. N.Y. Acad Sci.* 265:13 (1976); Salzar et al., *In Organization and Expression of Globin Genes*, A. R. Liss, Inc., New York at 313; Bernstein, *In Genetic Engineering: Principles and Methods*, Plenum Press, NY at 235; Dick et al., *Trends in Genetics* 2:165 (1986); Kiem, *Curr. Opin. Oncol.* 7;107–114 (1995). Viral vector transfer systems, such as retrovirus and adenovirus vectors, generally show a higher efficiency of transformation than DNA-mediated gene transfer procedures, such as $Ca_3(PO_4)_2$ precipitation and DEAE dextran. Retroviral vector transfer systems also have the capacity to integrate transferred genes stably into a wide variety of cell types. However, retroviruses require proliferation of target cells for the expression of the newly transferred gene. Other non-vial methods of gene transfer include microinjection, eletoporation, liposomes, chromosome transfer, and transfection techniques. See Cline, *Pharmacol. Ther.* 29:69–92 (1985). However, these non-viral vectors have a relatively low in vivo transduction efficiency.

Therefore, there exists a need in the art to develop gene therapy methods to induce vasodilation in the pulmonary circulation and to treat pulmonary hypertension.

SUMMARY OF THE INVENTION

This invention satisfies these needs in the art by providing a method of inducing pulmonary vasodilation comprising introducing a vector containing a nitric oxide synthase gene operably linked to an expression control element into the lungs of a patient in need of pulmonary vasodilation. The nitric oxide synthase can be a constitutively expressed or an inducible nitric oxide synthase gene. In specific embodiments of this invention, the pulmonary vasodilation is selective, the vector is an adenovirus vector, the nitric oxide synthase gene is the endothelial nitric oxide synthase gene, and this vector is transduced into lung tissue as an aerosol. In more specific embodiments, the resulting pulmonary vasodilation does not significantly affect systemic blood pressure or cardiac index.

This invention also relates to a method of treating pulmonary hypertension comprising overexpressing nitric oxide synthase in the lungs of a patient in need of treatment by introducing the nitric oxide synthase gene operably linked to an expression control element into the lungs of a patient in need of treatment. In specific embodiments, this method can be used to treat hypoxia-induced pulmonary hypertension, primary pulmonary hypertension, and pulmonary hypertension secondary to pulmonary or cardiac disease states.

This invention further relates to a pharmaceutical composition comprising the nitric oxide synthase gene operably linked to an expression control element and a means for transducing said gene into pulmonary tissue. In an exemplary embodiment, the pharmaceutical composition comprises AdCMVceNOS in admixture with a pharmaceutically acceptable carrier.

Further features, objects and advantages of the present invention will become more fully apparent to one of ordinary skill in the art from a detailed consideration of the following description of the invention when taken together with the accompanying drawings.

BRIEF DESCRIPTION OF THE FIGURES

FIG. 1 depicts the immunostaining for ceNOS in cultured rat fetal lung fibroblasts infected with AdCMVceNOS (A, top) and AdCMVHirudin (B, bottom). Abundant ceNOS immunoreactivity was observed in AdCMVceNOS infected cells, but not in AdCMVHirudin infected cells. The miciographs are at a 200-fold magnification.

FIG. 2 shows the expression of ceNOS in rat lungs. Protein extracts were obtained from the lungs of rats aerosolized with AdCMVceNOS (lane 2) and AdCMVβgal (lane 3). 70 μg samples of lung extracts were fractionated using SDS-PAGE and were transferred to nitrocellulose membranes. The presence of ceNOS was detected using a monoclonal antibody, and has an apparent molecular weight of 135 kDa. An extract from human umbilical vein endothelial cells was used as a positive control (lane 1). A monoclonal antibody directed against alpha-actin (42 kDa) was used to monitor the expression of unrelated protein.

FIG. 3 depicts ceNOS and β-galactosidase gene expression in the lungs of rats tans with AdCM- VceNOS and AdCMVβgal. AdCMVβgal transduced rat lungs show nuclear localized β-galactosidase staining in basal airway epithelial cells, alveolar epithelial cells, and adventitial cells of the small pulmonary vessels (A, 200-fold magnification). AdCMVceNOS transduced rat lungs show ceNOS staining in bronchial and alveolar epithelial cells, and in the endothelium of medium-sized and small pulmonary vessels (B, 200-fold magnification; C, 400-fold magnification). AdCMVβgal transduced rats show no ceNOS staining (D, 200-fold magnification).

FIG. 4 depicts cGMP production in RFL-6 cells. Cellular cGMP content was measured under baseline conditions and after infection with AdCMVceNOS in the absence and in the presence of L-NAME. Sodium nitroprusside (SNP) was used as a positive control and AdCMVHirudin, expressing the thrombin inhibitor, hirudin, was used as a second negative control for a virus containing an unrelated gene. The data depicted are means±SEM of five determinations, except for AdCMVHirudin, which are means±SEM of three determinations. * indicates $P<0.05$ vs. control, AdCMVceNOS=L-NAME, and AdCMVHirudin.

FIG. 5 compares hypoxic pulmonary vasoreactivity in AdCMVceNOS vs. AdCMVβgal transduced rats. Maximal changes in mean pulmonary artery pressure (mPAP, FIG. 5A, top panel) and total pulmonary resistance index (TPRI.

FIG. 6(A–B). FIG. 6 (SEQ. ID NO:5) depicts the nucleotide sequence of the endothelial isoform of the ceNOS gene.

DETAILED DESCRIPTION OF THE PREFERRED EMBODIMENTS

I. Definitions

Figure 1A:
FIG. 1(A–B).

In order to provide a clearer and more consistent understanding of the invention, the following definitions are provided.

As used herein "vasodilation" refers to a physical change in a blood vessel, which results in an increased blood flow capacity through the blood vessel. Vasodilation can either be active vasodilation or passive vasodilation. Active vasodilation is caused by a decease in the tonus of smooth muscle in the wall of the vessel. Passive vasodilation is caused by increased pressure in the lumen of the vessel.

As used herein "introduction" with reference to introducing nucleic acid into a cell, tissue, or organ refers to the transfer of genetic material into a cell using a viral or non-viral vector. This term is meant to encompass transduction, transformation, and transfection.

As used herein "transduction" refers to the transfer of genetic material into a cell by viral infection. Transduction normally results in the phenotypic expression of the genetic material introduced into the recipient cell.

As used herein "pulmonary hypertension" refers to elevated blood pressure in the pulmonary circulation Pulmonary hypertension can be either primary or secondary to pulmonary or cardiac disease. Typically, the pulmonary blood pressure in humans suffering from pulmonary hypertension is greater than 30 mm Hg systolic and greater than 12 mm Hg diastolic, or a mean pulmonary artery pressure in excess of 15–17 mm Hg.

As used herein "primary pulmonary hypertension" refers to pulmonary hypertension not caused by another underlying disease.

As used herein "secondary pulmonary hypertension" refers to pulmonary hypertension resulting from another underlying disease. Typically, the underlying disease causing secondary pulmonary hypertension is a pulmonary or cardiac disease.

As used herein "palliative therapy" refers to therapy that alleviates the symptoms of a disease without curing that disease.

As used herein "cardiac index" refers to the ratio of cardiac output to body weight.

As used herein "a pharmaceutical acceptable vehicle" is intended to include solvents, carriers, diluents and the like, which are used as additives to preparations of the recombinant DNA molecules containing the NOS gene of the invention so as to provide a carrier or adjuvant for the administration of such compounds.

As used herein "treatment" or "treating" is intended to include the administration of therapeutic compositions of the invention to a subject for purposes which may include prophylaxis, amelioration, prevention, or cure of a medical disorder, such as pulmonary hypertension.

As used herein "nitric oxide synthase" refers to an enzyme capable of catalyzing the formation of nitric oxide. For example, NOS can catalyze the formation of nitric oxide from the terminal guanidine nitrogen of arginine, with the stoichiometric production of citrulline. A nitric oxide synthase of this invention can be a constitutively expressed or inducible form of nitric oxide synthase.

As used herein "constitutive endothelial nitric oxide synthase" or "endothelial nitric oxide synthase" refers to a nitric oxide synthase having the enzymatic properties of the endothelial nitric oxide synthase encoded by a sequence depicted in FIG. 6, or a sequence having significant sequence homology with the sequence of FIG. 6. Typically, an endothelial nitric oxide synthase of this invention is encoded by a nucleic acid exhibiting greater than 90% sequence homology with the sequence of FIG. 6. In particular embodiments of this invention, an endothelial nitric oxide synthase of this invention is encoded by a nucleic acid exhibiting greater than 95% sequence homology with the sequence of FIG. 6.

As used herein a "vector" refers to a plasmid, phage, or other DNA molecule, which provides an appropriate nucleic acid environment for a transfer of a gene of interest into a host cell. A vector will ordinarily be capable of replicating autonomously in eukaryotic hosts, and may be further characterized in terms of endonuclease restriction sites where the vector may be cut in a determinable fashion. The vector may also comprise a marker suitable for use in identifying cells transformed with the cloning vector. For example, markers can be antibiotic resistance genes.

As used herein "operable linkage" refers to the position, orientation, and linkage between a structural gene and expression control element(s) such that the structural gene can be expressed in any host cell. The term "expression control element" includes promoters, enhancers, ribosome binding sites, etc.

II. Detailed Description

A. The Nitric Oxide Synthase Gene

This invention relates to gene therapy methods using the nitric oxide synthase gene to induce pulmonary vasodilation. In particular embodiments, this invention relates to methods of treating pulmonary hypertension.

The human endothelial isoform of the ceNOS gene has been cloned. See Janssens et al., *J. Biol. Chem.* 267:14519–14522 (1992). The ceNOS gene contains a 3609 bp open reading frame encoding a 1203 amino acid protein. The predicted molecular weight of this protein is about 133 kDa. At the amino acid level, this protein shares about 52 percent sequence homology with the neuronal isoform of NOS. This homology is most evident within regions corresponding to the flavin mononucleotide, flavin adenine dinucleotide, and NADPH binding sites, and less evident in the amino and carboxy terminal regions.

Plasmid hNOS3C containing the endothelial isoform of the ceNOS gene was deposited at the American Type Culture Collection on Jul. 17, 1996.

In addition to using this cloned ceNOS gene having the sequence of FIG. 6 to induce pulmonary vasodilation and treat pulmonary hypertension, this invention also relates to the use of ceNOS genes having similar but not identical sequences. Thus, this invention relates to the use of any ceNOS gene capable of synthesizing nitric oxide having a similar structure to the ceNOS gene depicted in FIG. 6. For example, due to the degeneracy of the genetic code, a ceNOS gene of this invention can encompass any nucleotide sequence encoding the amino acid sequence of ceNOS, as described in Janssens et al., supra. A ceNOS gene of this invention can also encompass genes encoding amino acid additions, substitutions, or deletions, so long as these changes do not significantly affect the structural or functional properties of the protein.

This invention also relates to the use of different classes or isoforms of NOS to induce pulmonary vasodilation and treat pulmonary hypertension. For example, inducible nitric oxide synthase (iNOS) can be used. Alternatively, the neuronal isoform (nNOS) can also be used. As with the ceNOS gene, this invention also relates to the use of iNOS and nNOS genes having similar but not identical sequences to those described supra at 3. For example, iNOS and nNOS genes useful to practice this invention can encode amino acid additions, substitutions, or deletions. The invention also encompasses the use of any iNOS or nNOS nucleotide sequence encoding the amino acid sequence of iNOS or nNOS, respectively.

Amino acid sequence deletions generally range from about 1 to 30 residues, more preferably 1 to 10 residues, and typically are contiguous. The deletions would typically be outside of the flavin mononucleotide, flavin adenine dinucleotide, and NADPH binding sites. For example, deletions may be in the amino or carboxy terminal regions of the protein.

Amino acid sequence insertions include amino and/or carboxy-terminal fusions of from one residue to polypeptides of essentially unrestricted length, as well as intrasequence insertions of single or multiple amino acid residues. Intrasequence insertions, i.e., insertions within the complete NOS molecule sequence, generally range from about 1 to 10 residues, more preferably 1 to 5. An example of a terminal insertion includes a fusion of a signal sequence, whether heterologous or homologous to the host cell, to the N-terminus or C-terminus of the molecule. A fusion sequence often facilitates the secretion of the NOS functional derivative from recombinant hosts.

A NOS of this invention also relates to a sequence in which at least one amino acid residue in the NOS molecule has been removed and a different residue inserted in its place. Such substitutions preferably are made in accordance with the following Table.

TABLE 1

| Original Residue | Exemplary Substitutions |
| --- | --- |
| Ala | Gly; Ser |
| Arg | Lys |
| Asn | Gln; His |
| Asp | Glu |
| Cys | Ser |
| Glu | Asp |
| Gly | Ala; Pro |
| His | Asn; Gln |
| Ile | Leu; Val |
| Leu | Ile; Val |
| Lys | Arg; Gln; Glu |
| Met | Leu; Tyr; Ile |
| Phe | Met; Leu; Tyr |
| Ser | Thr |
| Thr | Ser |
| Trp | Tyr |
| Tyr | Trp; Phe |
| Val | Ile; Leu |

Substantial changes in functional or immunological identity are made by selecting substitutions that are less conservative than those in Table 1, e.g., selecting residues that differ more significantly in their effect on maintaining (a) the structure of the polypeptide backbone in the area of substitution, for example, as a sheet or helical conformation, (b) the charge or hydrophobicity of the molecule at the target site, or (c) the bulk of the side chain. The substitutions that in general are expected to those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine.

B. Gene Transfer Vectors for the NOS Genes

Once an appropriate NOS gene has been selected, it must be inserted into an appropriate gene transfer vector for use in gene therapy. Appropriate gene transfer vectors include retroviral vectors, adenovirus vectors, and non-viral vectors that can be targeted to specific cell surface receptors for internalization. For example, Sendai virus (HVJ) can be used as a carrier for a cDNA-liposome complex.

Retroviral gene transfer vectors are retroviruses that have been rendered non-pathogenic by removal or alteration of viral genes so that little or no viral proteins are made in cells infected with the vector. Viral replication functions are provided through the use of packaging cells that produce viral protein but not infectious virus. Following infection of packaging cells with a retroviral vector, virions are produced that can infect target cells, but no further viral spread occurs. The major advantages of retroviral vectors for gene therapy include a high efficiency of gene transfer into replicating cells, the precise integration of the transferred genes into cellular DNA, and the lack of further spread of the sequences following transduction. However, the retroviral vectors are typically not made synthetically but should be produced by cultured cells, and these vectors are complex mixtures that are not purified to homogeneity after production. For a more detailed discussion of retroviral gene transfer vectors, see Miller, *Nature* 357:455–60 (1992).

Liposome mediated gene transfer can also be used with commercially available liposomes. However, the efficacy of gene transfer can be increased by combining the liposome with the HVJ virus.

Adenovirus gene transfer vectors are normally replication defective. These gene transfer vectors have the capacity to carry large segments of DNA, up to 8–10 kb. The adenovirus genome is about 36 kb in size. Other advantages include a very high titre ($10^{11}$ ml$^{-1}$), the ability to infect nonreplicating cells, and the ability to infect tissues in situ. Moreover, adenovirus gene transfer vectors do not integrate into the target chromosomal DNA.

An adenovirus gene transfer vector typically contains expression regulatory sequences such as promoters and enhancers. For example, the constitutive cytomegaloviruis (CMV) early gene promoter/enhancer and/or the SV40 polyadenylation signal sequence may be used. Other alternative expression regulatory sequences are known and could be selected by one skilled in the art. The NOS gene is then inserted into a plasmid containing appropriate regulatory elements using standard recombinant DNA techniques such that the regulatory elements are operably linked to the NOS gene. This expression cassette can then be inserted into a vector containing adenovirus sequences that permit homologous recombination with the adenovirus genome. By way of example, a suitable vector is pACCMVpLpA. This plasmid can then be cotransfected with a vector comprising the full-length adenovirus genome into a suitable host cell, which include transformed human embryonic kidney cells, containing an integrated copy of the left most 12% of the adenovirus 5 genome. The vector comprising the full-length adenovirus genome preferably contains an insert within the genome in order to exceed the packaging limit for adenovirus, rendering the full-length adenovirus containing vector replication defective.

Construction of recombinant adenovirus vectors is not only possible through homologous recombination in a suitable cell line, but also through direct in vitro ligation of fragments containing virion DNA and the recombinant viral vector. Suitable host cells for the cotransformation include human embryonic kidney cells, 911 cells (Introgene, b.v., Rijswijk, Netherlands) and PER 6 cells (Introgene). Alternatively, adenovirus vectors showing decreased immunogenicity can also be used.

Homologous recombination between the NOS containing plasmid and the plasmid containing the adenovirus genome results in an adenovirus genome of packageable size where the NOS gene has replaced a portion of the adenovirus genome necessary for viral replication. In specific embodiments of this invention, the adenovirus early region 1 is replaced by the cloned chimeric gene, rendering the virus replication defective. The resulting virus can be used as a gene transfer vector for the NOS gene. In addition, adenoviruses with insertions in the early region 3 (E3) and second generation adenoviral vectors with insertions into the early gene 2 or early gene 4 regions can be used for gene transfer purposes.

C. Introduction of the NOS Transfer Vector into Lung Tissue

A suitable NOS gene transfer vector of the invention can be delivered to the lungs using various delivery systems. For example, the gene transfer can occur either ex vivo or in vivo. For ex vivo gene transfer, macrophages can be transduced in vitro, and reintroduced into the patient. When gene transfer occurs in vivo, the vector can be introduced by intratracheal, intravenous, intraperitoneal, intramuscular, or intraarterial injections. In order to target the vector to lung tissue, adenovirus vectors that are selectively taken up by pulmonary endothelial cells may be used. Alternatively, a pulmonary tissue specific promoter can be used. However, aerosol delivery is preferred since it is non-invasive and results in deeper penetration of the material into the lungs. Aerosolized material can be deposited throughout the airways and alveoli of subjects to be treated. See Stribling et al., *Proc. Natl. Acad Sci (USA)* 89:11277–11281 (1992). Typically, the vector is diluted to the required concentration in an isotonic physiologic buffer solution. To optimize distal intro-alveolar delivery a surfactant can added to the solution.

The vector may also be combined with drugs that would lengthen the clearance time of the vector in the patient For example, effective concentrations of immunosuppressive agents, sufficient to lengthen the clearance time of the vector, such as cyclosporin or steroids could be used. The vector can also be combined with phosphodiesterase inhibitors such as Zaprinast See Cohen et al., *J. Clin. Invest.* 97:172–179 (1996).

The recombinant adenovirus vector comprising the NOS gene can be administered to patients in need of treatment as an aerosol. The concentration ranges would typically be $5 \times 10^7$ and $5 \times 10^9$ plague forming units (pfu) per ml. In specific embodiments of this invention, the concentration range would be from $5 \times 10^8$–$1 \times 10^9$ pfu/ml.

When the recombinant adenovirus vector comprising the NOS gene is administered to patients in need of treatment by intratracheal installation, concentration ranges administered are similar to the concentration ranges for aerosol administration.

The gene transfer vector can be formulated according to known methods to prepare pharmaceutically useful compositions, whereby the transfer vector is combined with a pharmaceutically acceptable carrier vehicle. These formulations may vary depending on the nature of the transfer vector, the mode of administration, and the indication. Suitable vehicles and their formulation are described, for example, in Remington's Pharmaceutical Science (18th ed. Mack Publ. Co. (1990)), incorporated herein by reference.

Having now generally described the invention, the same will now be more readily understood by reference to the following examples, which are provided by way of illustration and are not intended to be limiting.

EXAMPLES

Example 1

Transduction of Rat Fetal Lung Fibroblasts with AdCMVceNOS

To study whether high levels ceNOS protein expression could be achieved, rat fetal lung fibroblasts were grown to 60–70% confluence, infected with AdCMVceNOS or AdCMVHirudin, fixed, and stained with a monoclonal anti-ceNOS antibody.

In order to construct AdCMVceNOS, a 3.7 kb EcoRI/BamHI fragment of the human endothelial nitric oxide synthase cDNA, Janssens, S. P. et al., *J. Biol. Chem.* 267:14519–14522 (1992), was constructed by ligating a 3.4 kb EcoRI/NcoI fragment to a 0.3 kb PCR fragment containing an additional 3'-BamHI restriction site. The latter was amplified using a (SEQ. ID NO:1) 5'-CGGCGATGTTACCATGGCAACCAACGT-3' primer corresponding to the NcoI site at position 3398 and a (SEQ. ID NO:2) 5'-CGGATCCCGGCTCTCAGGGGCTGTTGGTG-3' primer and including an additional BamHI site at the 3' end of the cDNA.

For the recombinant virus construction, the 3.7 kb fragment comprising the entire protein coding region of ceNOS was cloned between the immediate early CMV promoter/enhancer and the SV40 polyadenylation signal of the bacterial plasmid pACCMVpLpA. Gomez-Foix, A. et al., *J. Biol. Chem.* 267:25129–25134 (1992). pACCMVpLpA was obtained from Dr. R. D. Gerard, Center for Transgene Technology and Gene Therapy, Leuven, Belgium. This plasmid contains the E1A-deleted sequences of type 5 adenovirus, including the origin of replication, the packaging signal, the pUC19 polylinker, and the strong enhancer/promoter of the immediate early genes of cytomegalovirus (CMV). A recombinant adenovirus was generated by homologous recombination with pJM17, obtainable from Microbix Biosystems, Inc., Toronto, Ontario, Canada, a bacterial plasmid containing the full-length adenoviral genome, following cotransfection in E1A-transformed human embryonic kidney cells. These cells art available from the American Type Culture Collection, Rockville, Md. and the Microbix Biosystems, Inc., Toronto, Ontario, Canada.

The presence of the human ceNOS insert in virion DNA isolated from infected 293 cells was confirmed by PCR analysis using the (SEQ. ID NO:3) 5'-CGGCGATGTTACCATGGCAACCAACGT-3' primer complementary to the ceNOS 3'-NADPH-adenine site and the (SEQ. ID NO:4) 5'CTCTGTAGGTAGTTTGTCCA-3' primer corresponding to the SV40 splice/polyA site. Southern blot analysis of recombinant viral DNA isolates probed with the pruner complementary to the ceNOS 3'-NADPH-adenine site was also performed. ceNOS-containing viral isolates were amplified on confluent 293 cells and, after appearance of cytopathic effects, isolated, precipitated, and concentrated by discontinuous CsCl gradient. Gerard, C. and Meidell, R., Adenovirus vectors in DNA cloning—A practical approach, in *Mammalian Systems*, Hames, B. D. & Glover, D., eds., Oxford University Press, Oxford, England (1995). These viral isolates were named AdCMVceNOS. Viral titers were determined by infection of monolayers of 293 cells with serial dilutions of the recombinant adenovirus.

Recombinant adenovirus carrying the LacZ gene encoding a nuclear-localizing variant of the *E. coli* β-galactosidase gene were prepared, amplified and titered as for AdCMVceNOS. See Herz, J. & Gerard, R. D., *Proc. Natl. Acad. Sci. USA* 90:2812–2816 (1993). Similarly, a viral construct containing the cDNA of the thrombin inhibitor hirudin was prepared for use as a control virus. For all in vivo studies, viral titers were adjusted to $5 \times 10^9$ pfu/ml. For transduction of rat fetal lung fibroblasts, multiplicities of infection (MOI) of 10 and 100 were selected, since a higher MOI was associated with cytopathic effects.

To detect ceNOS protein in the transduced rat fetal lung fibroblasts, the rat fetal lung fibroblasts (RFL-6) were cultured in DMEM supplemented with 10% fetal bovine serum (GIBCO), 50 units/ml penicillin, and 50 mg/ml streptomycin. The cells were grown in chamber slides (Nunc, Naperville, Ill.) to about 60% confluence and infected with AdCMVceNOS and AdCMVHirudin diluted in DMEM with 2% fetal bovine serum at 10 and 100 pfu/cell. After 12 hours, the viral suspension was removed and the cells were maintained in culture for 3 days. The presence of the ceNOS gene product was detected by immunostaining. Three days following in vitro infection with the adenoviral vectors, the cells were washed with phosphate-buffered saline, fixed for 20 minutes in 4% paraformaldehyde and washed twice in 1 mM Tris, 0.9% NaCl, 0.1% Triton X-100, pH 7.6 (Tris-buffered saline, TBS). Cells were pre-incubated with swine serum at a 1:5 dilution in TBS for 45 minutes and exposed overnight to anti-ceNOS pAB, a rat polyclonal antibody that recognizes human ceNOS (Transduction Laboratories, Exeter, UK) at a concentration of 2 mg/ml. After a one-hour incubation with horseradish peroxidase-labeled swine anti-rabbit second antibody, Prosan, diluted 1:50, and pre-absorbed overnight with 10% rat serum and 3% bovine serum albumin, antibody binding was visualized with diaminobenzedine tetrahydrochloride in 0.1 M Tris buffer, pH 7.2, containing 0.01% $H_2O_2$. Harris' hematoxylin was used as counterstain and slides were dehydrated and mounted with dePex mountant medium (Prosan, Gent, Belgiun).

Figure 1B:
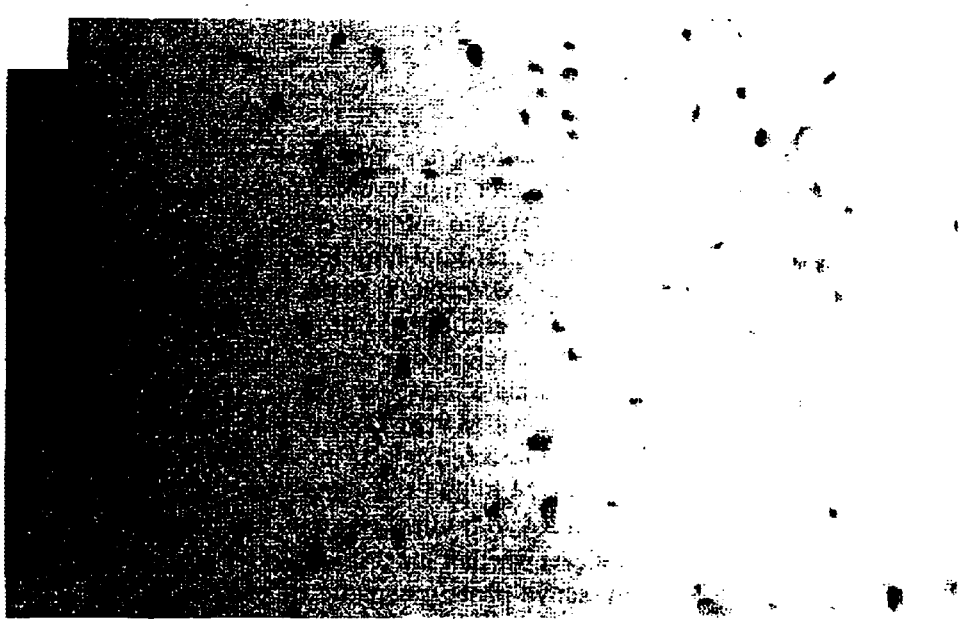

After 3 days, abundant ceNOS was observed in the AdCMVceNOS but not in the AdCMV hirudin-infected cells. See FIG. 1. ceNOS expression was detectable after 24 hours, and the number of cells staining positive peaked at 3 days following infection.

Example 2

Measurement of cGMP Levels in Transduced Rat Fetal Lung Fibroblasts

RFL-6 cells from the American Type Culture Collection, Rockville, Md., which contain abundant soluble guanylate cyclase, were grown to 90% confluence in 12-well tissue-culture plates ($10^5$ cells/well) and infected for 4 hours with either AdCMVceNOS or AdCMVHirudin at 100 pfu/cell or medium only (DMEM with 2% fetal bovine serum) [MOl=100]. Following infection, cells were cultured for 3 days in DMEM with 10% fetal bovine serum. Cells were pretreated for 10 min. with 0.3 mM 3-isobutyl-1-methylxanthine (IBMX) to inhibit phosphodiesterase activity in the presence of the calcium ionophore A23187 (2 mM) to stimulate ceNOS activity. 1 mM sodium nitroprusside for 5 minutes was used as a positive control. Intracellular cGMP was extracted in ice-cold 15% trichloroacetic acid (TCA), pH 4.0. TCA was extracted in $H_2O$-saturated ether and, following lyophilization, cGMP was quantitated by a commercial enzyme-immuno assay (Amersham Lifescience, Gent, Belgium). The specificity of cGMP formation following soluble guanylate cyclase stimulation by transduced NOS was confirmed by inhibition with 0.5 mM $N^G$-nitro-L-arginine methyl ester (L-NAME).

Figure 2:
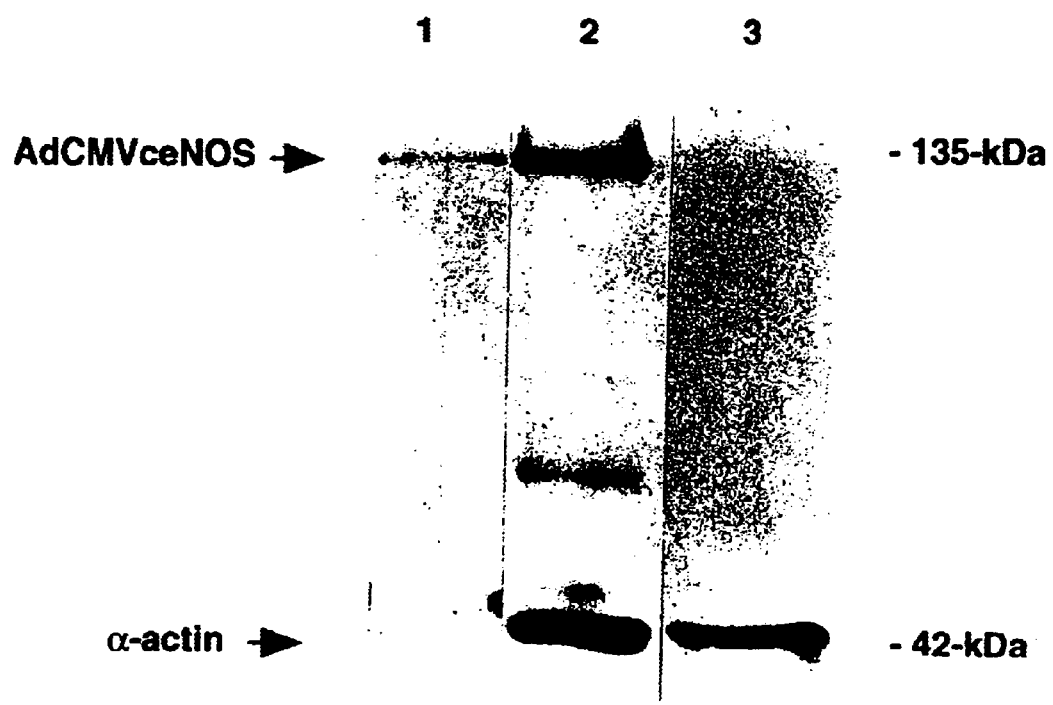
FIG. 2.

Intracellular cGMP was measured in cells exposed to the calcium ionophore A23187 (2 mM) and IBMX. cGMP levels did not differ between uninfected RFL-6 cells and RFL-6 cells infected with AdCMVHirudin. cGMP levels were markedly increased in RFL-6 cells infected with AdCMVceNOS, and in cells exposed to sodium nitroprusside, a NO donor compound. See FIG. 2. Preincubation of RFL-6 cells with 0.5 mM L-NAME for 30 minutes markedly reduced cGMP levels in AdCMVceNOS-infected cells. The L-NAME-inhibitable increase in cGMP levels in AdCMVceNOS-infected RFL-6 cells suggested that the transgene encoded a biologically active NOS.

Example 3

Transduction of Lung Tissue After Aerosolization of Recombinant AdCMVβgal and AdCMVceNOS To achieve high levels of transgene expression in peripheral pulmonary tissues, recombinant adenoviruses were aerosolized in vivo in rat lungs during mechanical ventilation. Recombinant adenovirus carrying the LacZ gene was used to study the distribution of transgene expression.

Wistar rats (300–350 grams body weight) were anesthetized by intraperitoneal injection of pentobarbital (50 mg/kg), intubated with a polyethylene tube (number PE-240 tubing; 1.67 mm ID), and mechanically ventilated with room air (Model 683; Harvard Apparatus, South Natick, Mass.). During mechanical ventilation, 600 μl solution of recombinant adenovirus (AdCMVβgal and AdCMVceNOS, $5 \times 10^9$ pfu/ml) were aerosolized into the lungs via a silastic catheter introduced via a midline neck incision into the trachea distal from the endotracheal tube. Using a tuberculin syringe, a total volume of 600 μl viral solution was administered drop by drop during the inspiratory phase of the ventilatory cycle (50 μl/10 minutes). Tidal volume was set at 2.5 ml, and frequency at 60/minute. After viral delivery, the catheter was removed from the trachea. Control rats were given an equal volume of sterile saline solution. No side effects were observed during aerosol delivery or following extubation.

Figure 3B:
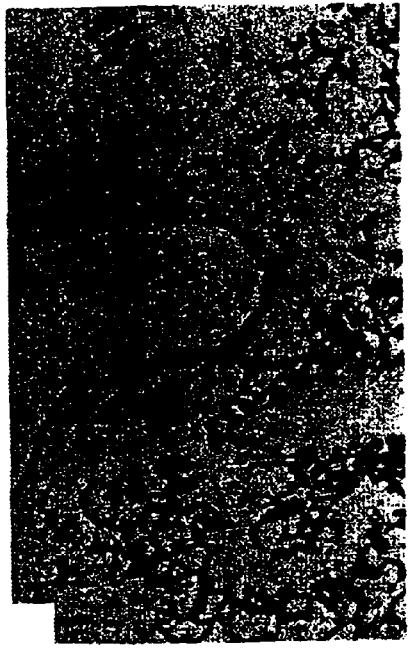
FIG. 3(A–D).
Figure 3A:

Four days after administration of AdCMVβgal into the lungs, animals were sacrificed by an overdose of pentobarbital, and the lungs were perfused and fixed through the airways in 4% (wt/vol) formaldehyde. 2 mm-thick segments from the central and peripheral areas of all lobes were incubated in 20% sucrose overnight, overlaid with O.C.T. compound and frozen in liquid nitrogen. Seven micrometer cryostat sections were mounted on poly-L-lysine-coated slides, and the presence and distribution of the LacZ gene was detected using β-galactosidase staining (5 mmol/L $K_4Fe(CN)_6$, 5 mmol/L $K_3Fe(CN)_6$, 1 mmol/L $MgCl_2$ and 1 mg/ml 5-Bromo-4-chloro-3-indolyl-β-D-galactopyranoside (Boehringer Mannheim GmbH, Germany) in PBS) for 4–6 hours, and counter-stained with eosin. To estimate gene transfer efficiency in the histological sections, positive cells were identified by their nuclear blue coloration. AdCMVβgal-infected lungs showed diffuse transduction of airway epithelial cells, alveolar lining cells, and adventitial cells in medium and small-sized pulmonary vessels after 5 days (see FIG. 3A).

To measure the localization of ceNOS immunoreactivity in AdCMVceNOS-transduced lung tissue, lungs from AdCMVceNOS-infected animals were perfused through the pulmonary artery with PBS, and 4% formaldehyde was instilled into the airways. Lungs were divided in small central and peripheral segments corresponding to the different lobes, and the segments were overlaid with O.C.T. compound and frozen in liquid nitrogen. Seven μm cryostat sections were mounted on slides, washed twice with TBS and blocked with normal rat serum, diluted 1:5 in TBS for 45 minutes. The sections were incubated overnight with the anti-ceNOS antibody (2 mg/ml) followed by incubation for 1 hour with a rabbit anti-mouse IgG peroxidase conjugate (dilution 1:50; preabsorbed overnight at 4° C. with 10% preimmune rat serum and 3% bovine serum albumin). Antibody binding was visualized with 3,3'-diaminobenzadine tetrahydrochloride (DAB, Sigma Chemicals) in 0.1 M Tris buffer, pH 7.2, containing 0.01% $H_2O_2$. Sections were counter-stained with Harris' hematoxylin, dehydrated, and mounted with dePex-mountant medium.

Figure 3D:
Figure 3C:

The efficacy and distribution of ceNOS expression in the lungs following aerosolization of AdCMVceNOS was studied at various times (3, 4, 5, 8 and 12 days) after gene transfer by immunostaining with monoclonal antibodies directed against human ceNOS. Diffuse ceNOS immunostaining was observed in large airways, lung parenchyma, and endothelial cells of the medium-sized and small pulmonary vessels. See FIGS. 3B and 3C. The intensity of staining was maximal after 5 days, but was still detected after 2 weeks. In control and AdCMVβgal-treated rats, no ceNOS immunoreactivity was detected in large airways, alveolar epithelial cells, or in small pulmonary vessels. See FIG. 3D. Endogenous ceNOS immunoreactivity was predominantly detected in endothelial cells of large, fully muscular vessels. There was little variation in the staining pattern between animals infected with AdCMVceNOS. Infection with a titer of $5 \times 10^9$ pfu/ml AdCMVceNOS was not associated with any significant pulmonary infiltrates and did not affect body weight.

Example 4

Activation of the Inducible Form of NOS (iNOS) by Transduction of AdCMVceNOS

Cytokines released during local inflammatory reactions or in response to adenoviral infection could activate the inducible isoform of NOS (iNOS). Therefore the effect of gene transfer and the associated immune response against adenovirus on the stimulation of iNOS gene expression in rat lungs was investigated. No iNOS immunoreactivity was observed with a specific anti-iNOS antiserum (Transduction Laboratories) on sections from AdCMVceNOS or AdCMVβgal-tread rats. These results show that recombinant adenovirus infection itself does not appreciably stimulate NOS production via inflammation and induction of the inducible isoform of NOS.

Example 5 ceNOS Protein Levels in Adenovirus-Infected and Control Lungs ceNOS protein levels in adenovirus-infected and control lungs were measured by immunoblot analysis of extracts from control, AdCMVβgal, and AdCMVceNOS-treated rat lungs.

Expression of ceNOS in rat lungs was assessed on day 4 after gene transfer. Animals were sacrificed and the lungs were excised and processed immediately or quick-frozen in liquid nitrogen. To extract total protein, lungs were homogenized in ice-cold buffer (5 mM Hepes, pH 7.9; 26% glycerol (v/v); 1.5 mM $MgCl_2$; 0.2 mM EDTA; 0.5 mM DTT; 0.5 mM phenylmethanesulfonyl fluoride (PMSF); and 300 mM NaCl) and incubated on ice for 30 minutes. After centrifugation at 100,000 g at 4° C. for 20 minutes, the supernatant containing crude enzyme preparations was mixed with an equal volume of 2% SDS/1% β-mercaptoethanol and fracionated using 8% SDS/PAGE (70 μl/lane). Proteins were then transferred to a nitrocellulose membrane (Hybond-ECL, Amersham Lifesciences, Gent, Belgium) by semi-dry electroblotting for one hour. The membranes were blocked by incubating for one hour at room temperature with blotto-Tween (5% nonfat dry milk, 0.1% Tween-20) and incubated with a primary monoclonal mouse anti-ceNOS IgGl antibody (mAb, 0.25 mg/ml, dilution 1:1000, Transduction Laboratories, Exeter, UK). Bound antibody was detected with horseradish peroxidase-labeled rat anti-mouse IgG second antibody (Prosan, dilution 1:2000 in Blotto/Tween) and visualized using enhanced chemiluminescence (ECL, Amersham, Gent, Belgium).

Figure 4:
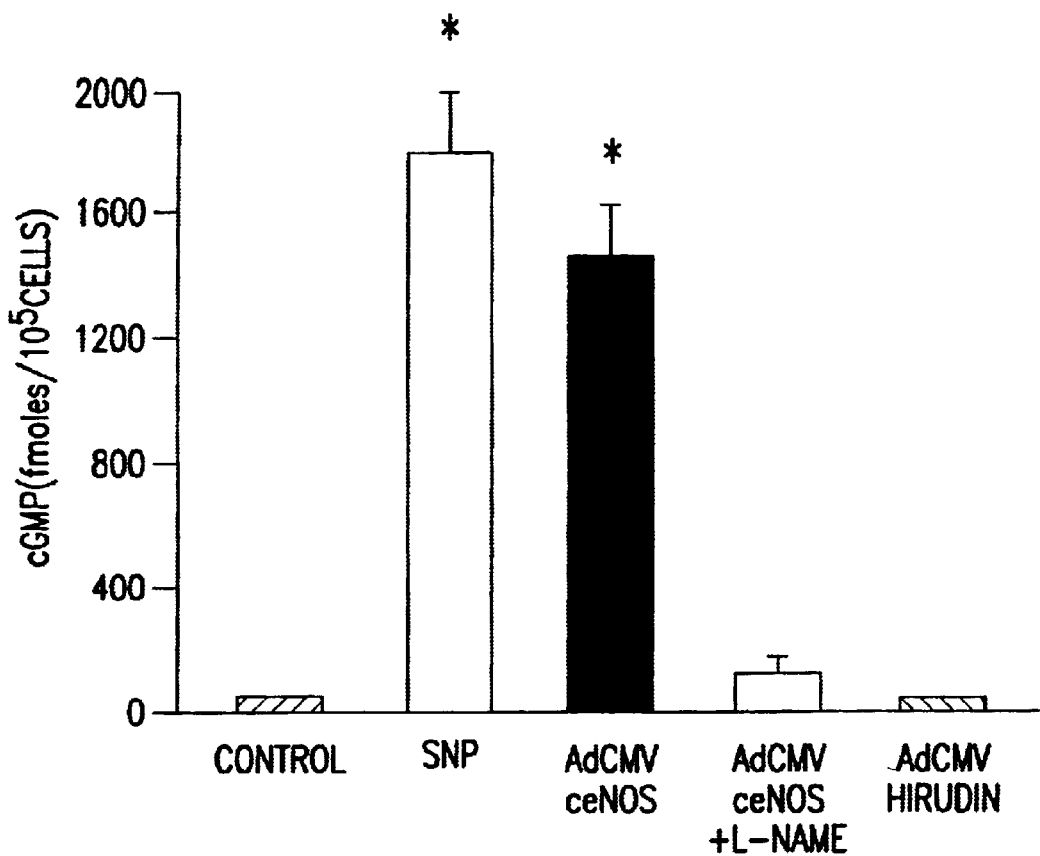
FIG. 4.

The antibody detected abundant levels of the 135 kDa protein in the lung extracts of rats 4 days after treatment with AdCMVceNOS (FIG. 4). Only very low levels were detected after aerosolizaton of AdCMVβgal, or in lung extracts from untreated control rats.

Example 6 ceNOS Enzymatic Activity in Adenovirus-Infected and Control Lungs ceNOS enzymatic activity as defined by [$^3$H]L-arginine to [$^3$H]L-citrulline conversion was measured in extracts from AdCMVβgal and AdCMVceNOS transduced lungs.

To measure ceNOS enzymatic activity, L-arginine to L-citrulline conversion was assayed in pulmonary extracts using a modification of the method described by Xue et al., Amer. J. Phys. 267:L667–L678 (1994). Lung protein extracts prepared as described above were purified by affinity chromatography on 2',3'-ADP Sepharose and incubated for 30 minutes at 37° C. in a solution of 10 mM L-[2,3-$^3$H] argenine (59 Ci/mmol:1 Ci=37 Gbq), 1 mM NADPH, 100 nM calmodulin, 2 mM $CaCl_2$, 200 μM tetrahydrobiopterin in a final volume of 1 ml. To inhibit NOS activity, duplicate samples were incubated in the presence of 0.5 mM L-NAME. The reaction was stopped by adding 1 ml of stop buffer (2 mM EGTA, 2 mM EDTA, 20 mM Hepes buffer, pH 5.5) to 200 μl aliquots of the reaction mixture. The total volume was then applied to a 1 ml Dowex AG 50WX-8 column ($Na^+$ form, Bio-Rad Laboratories, Nazareth Eke, Belgium) preequilibrated with the stop buffer. L-[2,3-$^3$H] citrulline was eluted with 2 ml of distilled water and the radioactivity was determined by liquid scintillation counting. Enzyme activity was expressed as citrulline production in $pmol \cdot minutes^{-1} \cdot mg\ proteins^{-1}$.

[$^3$H]L-citrulline formation was 86% greater in lung acts from AdCMVceNOS treated rats compared to AdCMVβgal treated animals, and this increased conversion was blocked in the presence of L-NAME. Simultaneously, biological activity of the expressed ceNOS was evaluated by measuring intrapulmonary cGMP.

Example 7 cGMP Levels in Adenovirus-Infected and Control Lungs

Intrapulmonary cGMP levels were measured in extracts from AdCMVceNOS, AdCMVβgal, and control lung. For cGMP determinations lungs were frozen in liquid nitrogen and 400 to 700 mg tissue samples subsequently homogenized in 1 ml icecold 6% trichloroacetic acid (TCA), pH 4.0. The sample was then centrifuged at 10,000×g for 15 minutes at 4° C. The supernatant was transferred to a 30 ml glass centrifuge tube and TCA was ether extracted 4 times. A 500 μl aliquot of the sample was then lyophilized, resuspended in 500 μl of 0.05M sodium acetate buffer (pH 5.8) and assayed for cellular cGMP utilizing a nonradioactive enzyme-immunoassay kit (Amersham Life Science). Pulmonary cGMP levels were described as picomoles cGMP per mg of TCA precipitatiable protein.

cGMP levels were about 10-fold greater in AdCMVceNOS transduced lungs compared to control lungs (59±9 pmol/mg protein vs. 7±1 pmol/mg protein and 3±1 pmol/mg protein, respectively, P<0.05).[2]

[2] Analysis of variance (ANOVA) in the Examples was determined by the Student-Neumann-Keuls post test to determine significant differences in multiple comparison testing ween groups. All values are expressed as means±SEM. For all experiments, statistical significance was assumed at P<0.05.

Example 8

Aerosolization of Recombinant AdCMVceNOS Attenuates Hypoxia-induced Pulmonary Vasoconstriction The effect of increased production of NO following AdCMVceNOS gene transfer on hypoxic pulmonary vasoconstriction was investigated.

After recovery from the aerosol gene delivery procedure, rats were maintained in room air for three days and reanesthesitized on the fourth day after gene transfer. To measure pulmonary artery pressure (PAP), a silastic catheter (0.30 mm ID, 0.64 mm OD) was introduced into the right jugular vein and advanced through the right atrium and ventricle into the pulmonary artery. To measure systemic arterial pressure, a 2 F catheter was positioned in the right carotid artery. Both carotid arterial and pulmonary artery catheters were connected to a pressure transducer (Model AA 016 Baxter, Uden, Holland), a display oscilloscope (Press Ampl. 863, Siemens, Germany) and a thermal recorder (Mingograf 82, Siemens, Solna, Sweden). The position of the pulmonary artery catheter was verified by the characteristic pressure tracing on the oscilloscope and was confirmed by autopsy. Electronically meaned PAP and right ventricular systolic pressures were recorded Cardiac output was measured by the thermodilution technique which was validated in rodents in previous studies. See Janssens et al., J. Applied Physiol. 77:1101–1108 (1994). Briefly, a 1.5 F thermodilution probe was inserted in the thoracic aorta via the right carotid artery and connected to a thermal dilution computer (Model REF-1, Edwards, USA), and a strip-chart recorder. Through the silastic pulmonary artery catheter, 0.15 ml saline was injected and cardiac output was read directly from the computer display. All values were measured in triplicate and varied <15%. Cardiac index (CI) was defined as the ratio of cardiac output over body weight in kilograms ($ml \cdot min^{-1} \cdot kg^{-1}$). Total pulmonary vascular resistance index (TPRI) was computed by dividing mean pulmonary artery pressure by cardiac index ($mm\ Hg \cdot min^{-1} \cdot ml^{-1} \cdot kg^{-1}$).

Rats were initially mechanically ventilated with room air and baseline PAP, systemic blood pressure, and cardiac output were recorded. To study the hypoxic pulmonary vasoconstrictor response, rats were ventilated with 10% $O_2$, 90% $N_2$, and PAP was monitored continuously for 25 minutes. After 5, 15, and 25 minutes of hypoxia, cardiac output was measured. Rats were then ventilated with room air and hemodynamic measurements were repeated after 20 minutes.

Figure 5A:
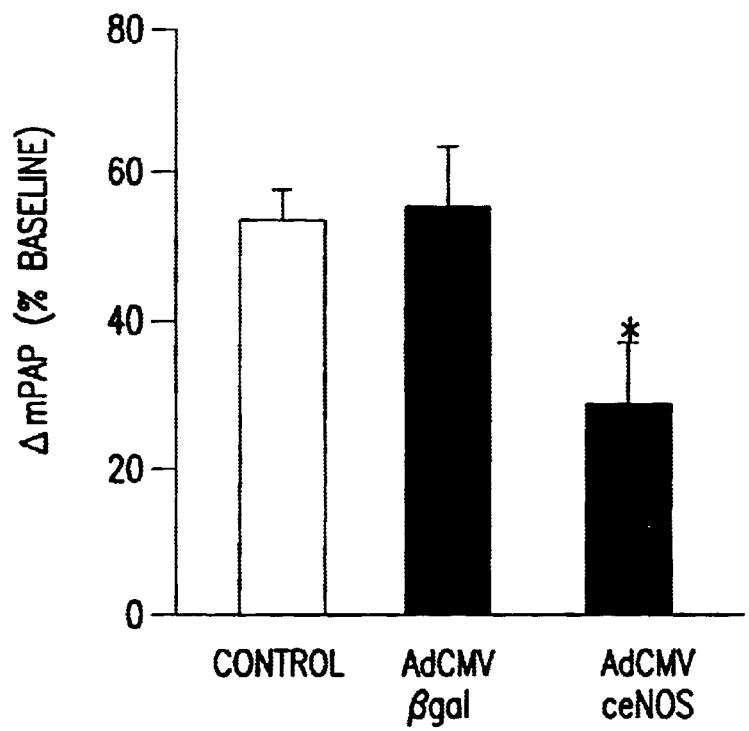
FIG. 5(A–B).
FIG. 5B, bottom panel) are depicted for uninfected rats (open bars, n=8), AdCMVβgal transduced rats (dashed bars, n=8) and AdCMVceNOS transduced rats (closed bars, n=8) during a 25 min. acute hypoxic challenge. Pressure and resistance changes are expressed as a percentage of baseline. * indicates $P<0.05$ vs. controls and AdCMVβgal. Values are mean±SEM.
Figure 5B:
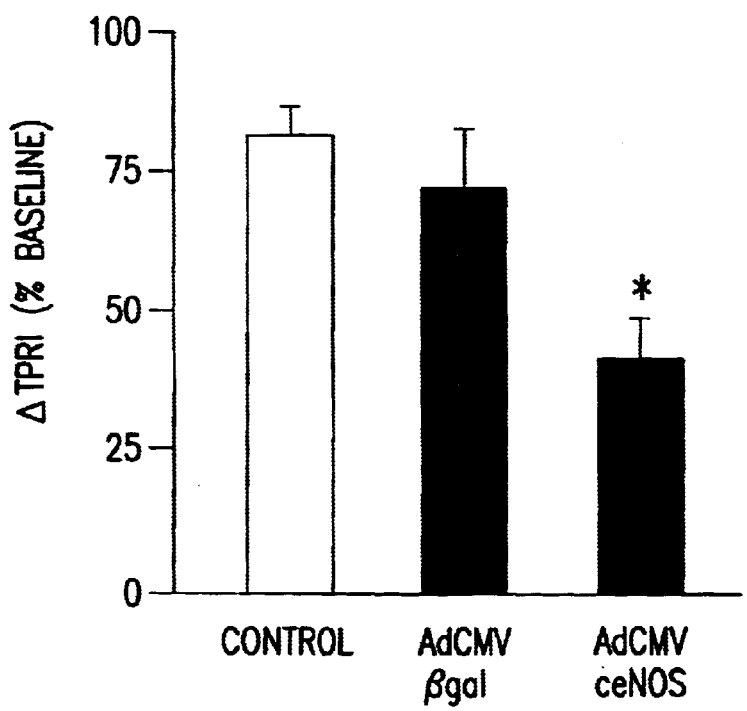

During acute hypoxia, PAP increased from 18±1 mm Hg to 27±1 and 28±1 mm Hg in saline control and AdCMVβgal transduced rats, respectively. In contrast, the rise in PAP was markedly attenuated in AdCMVceNOS transduced rats (23±2 mm Hg, P<0.05) and was significantly decreased as early as 5 minutes of hypoxia See FIG. 5, left panel. Cardiac index did not differ between AdCMVceNOS treated rats and AdCMVβgal infected rats 185±15 ml/min/kg vs. 176±18 ml/min/kg, respectively). The reduction in total pulmonary resistance index (TPRI) during acute hypoxia in AdCMVceNOS treated rats was to 0.157 $mm\ Hg \cdot ml^{-1} \cdot min^{-1} \cdot kg^{-1}$ and to 0.122 $mm\ Hg \cdot ml^{-1} \cdot min^{-1} \cdot kg^{-1}$ for AdCMVβgal and saline control rats, respectively. This reduction was therefore due to a direct pulmonary vasodilatory effect rather than an indirect effect on cardiac output. See FIG. 5, right panel. Systemic blood pressure was similar in AdCMVceNOS treated and in AdCMVβgal treated rats (153±6 mm Hg vs. 150±6 mm Hg, respectively, n=4). Taken together, aerosolization of AdCMVceNOS and the resulting overexpression of the ceNOS gene product significantly reduced acute hypoxic vasoconstriction without affecting systemic blood pressure or cardiac index.

ceNOS gene transfer thus locally produces NO which selectively vasodilates pulmonary vessels in a fashion similar to that observed with NO gas therapy in hypoxic newborn rats and in human volunteers breathing 12% $O_2$ in $N_2$. Frostell et al., Anesthesiology 78:427–435 (1993). Inhaled NO did not affect pulmonary hemodynamics during room air breathing and caused no systemic hemodynamic effects, possibly because any NO which diffuses into the blood stream is rapidly inactivated by hemoglobin. Rimar et al., *Circulation* 88:2884–2887 (1993). Similarly, AdCM-VceNOS aerosol did not affect systemic blood pressure. However, NO gas inhalation only has an immediate and shortlasting effect on pulmonary hemodynamics, and requires continuous administration. Pepke-Zaba et al., *Lancet* 338:1173–1174 (1991). By contrast, these results demonstrate that a single aerosol does of AdCMVceNOS was able to attenuate hypoxic pulmonary vasoconstriction even when the hypoxic challenge was applied 4 to 7 days after gene delivery. Thus, these results are indicative that ceNOS expression in lungs is safe and has clinical applications as adjunctive treatment in some pulmonary hypertensive disease states responsive to inhaled NO, including persistent pulmonary hypertension of die newborn, perioperative pulmonary hypertension, and adult respiratory distress syndrome.

What is claimed is:

1. A method of inducing pulmonary vasodilation comprising:

introducing an aerosolized adenoviral vector comprising a nitric oxide synthase gene operably linked to an expression control element into the lungs of a mammal in need of pulmonary vasodilation;

wherein the introduction of said vector into the lungs of said mammal results in pulmonary vasodilation that does not significantly affect systemic blood pressure or cardiac index.

2. The method of inducing pulmonary vasodilation as claimed in claim 1, wherein said mammal is a human.

3. The method of inducing pulmonary vasodilation as claimed in claim 2, wherein said nitric oxide synthase gene is the endothelial nitric oxide synthase gene.

4. The method or inducing pulmonary vasodilation as claimed in claim 3, wherein said endothelial nitric oxide synthase gene is transduced into the lungs of said human in a viral vector.

5. The method of treating pulmonary hypertension as claimed in claim 1 wherein said adenovirus vector is AdCMVceNOS.

6. A method of treating pulmonary hypertension comprising:

introducing an aerosolized adenoviral vector comprising nitric oxide synthase gene operably linked to an expression control element into the lungs of a mammal in need of treatment for pulmonary hypertension;

wherein the introduction of said vector into the lungs of said mammal results in pulmonary vasoldilation that does not significantly affect systemic blood pressure or cardiac index.

7. The method of treating pulmonary hypertension as claimed in claim 6, wherein said mammal is a human.

8. The method of treating pulmonary hypertension as claimed in claim 7, wherein said nitric oxide synthase gene is the endothelial nitric oxide synthase gene.

9. The method of treating pulmonary hypertension as claimed in claim 8, wherein said pulmonary hypertension is primary pulmonary hypertension.

10. The method of treating pulmonary hypertension as claimed in claim 8, wherein said pulmonary hypertension is secondary pulmonary hypertension associated with cardiac or pulmonary disease.

11. The method of treating pulmonary hypertension as claimed in claim 8, wherein said endothelial nitric oxide synthase gene is transduced into the lungs of said human in a viral vector.

12. The method of treating pulmonary hypertension as claimed in claim 6, wherein said adenovirus vector is AdCMVceNOS.

13. A method of inducing pulmonary vasodilation comprising: administering, by aerosol administration, to a mammal in need of pulmonary vasodilation an effective amount of the pharmaceutical composition comprising a nucleic acid encoding a nitric oxide synthase gene operably linked to a pulmonary issue specific expression control element, an adenoviral vector, a pharmaceutically acceptable carrier vehicle, and an effective amount of at least one drug selected from the group consisting of an immunosuppressive agent and a phosphodiesterase inhibitor; wherein inducing said pulmonary vasodilation does not significantly affect systemic blood pressure or cardiac index.

14. The method of inducing pulmonary vasodilation as claimed in claim 13, wherein said mammal is a human.

* * * * *